(12) United States Patent
Azer et al.

(10) Patent No.: US 8,728,007 B2
(45) Date of Patent: May 20, 2014

(54) METHOD AND SYSTEM FOR MANAGING PATIENT DATA

(75) Inventors: Anwar A Azer, Stoneham, MA (US); Ramon E Benet, Westford, MA (US)

(73) Assignee: Instrumentation Laboratory Company, Bedford, MA (US)

( * ) Notice: Subject to any disclaimer, the term of this patent is extended or adjusted under 35 U.S.C. 154(b) by 4 days.

(21) Appl. No.: 13/108,348

(22) Filed: May 16, 2011

(65) Prior Publication Data

US 2011/0295091 A1 Dec. 1, 2011

Related U.S. Application Data

(62) Division of application No. 11/044,626, filed on Jan. 27, 2005, now Pat. No. 7,972,279.

(51) Int. Cl.
*A61B 5/00* (2006.01)

(52) U.S. Cl.
USPC ........................................................ 600/575

(58) Field of Classification Search
USPC ........................................................ 600/575
See application file for complete search history.

(56) References Cited

U.S. PATENT DOCUMENTS

| | | |
|---|---|---|
| 3,874,850 A | 4/1975 | Sorensen et al. |
| 3,960,497 A | 6/1976 | Acord |
| 4,271,474 A | 6/1981 | Belanger et al. |
| 4,481,804 A | 11/1984 | Eberhard et al. |
| 4,734,184 A | 3/1988 | Burleigh et al. |
| 4,787,398 A | 11/1988 | Garcia et al. |
| 4,975,647 A | 12/1990 | Downer et al. |
| 5,022,980 A | 6/1991 | Tanaka et al. |
| 5,061,631 A | 10/1991 | Calabrese |
| 5,067,093 A | 11/1991 | Przybylowicz et al. |
| 5,070,023 A | 12/1991 | Calabrese |
| 5,103,179 A | 4/1992 | Thomas et al. |
| 5,112,454 A | 5/1992 | Tanaka et al. |
| 5,198,093 A | 3/1993 | Sydlowski et al. |
| 5,339,821 A | 8/1994 | Fujimoto |
| 5,766,432 A | 6/1998 | Dunn et al. |
| 5,904,708 A | 5/1999 | Goedeke et al. |
| 5,966,676 A | 10/1999 | Fujiwara et al. |
| 5,976,085 A | 11/1999 | Kimball et al. |

(Continued)

FOREIGN PATENT DOCUMENTS

| DE | 32 20 327 | 12/1982 |
|---|---|---|
| DE | 195 46 535 | 6/1997 |

(Continued)

OTHER PUBLICATIONS

"The Universal Connectivity Standard for Point-of-Care", Connectivity Industry Consortium, AACC Milestone Status, San Francisco, Jul. 22, 2000.*

(Continued)

*Primary Examiner* — Max Hindenburg
*Assistant Examiner* — Renee Danega
(74) *Attorney, Agent, or Firm* — Burns & Levinson LLP

(57) ABSTRACT

The present invention relates to a method and apparatus for managing patient data. In one aspect, the invention relates to a system for managing patient data having many instruments. The instruments have a sampling member for sampling a body fluid from a patient and are in direct communication with at least one other instrument.

23 Claims, 5 Drawing Sheets

(56) References Cited

U.S. PATENT DOCUMENTS

| | | | |
|---|---|---|---|
| 6,088,608 | A | 7/2000 | Schulman et al. |
| 6,123,827 | A | 9/2000 | Wong et al. |
| 6,136,607 | A | 10/2000 | Conlon et al. |
| 6,192,320 | B1 | 2/2001 | Margrey et al. |
| 6,512,986 | B1 | 1/2003 | Harmon |
| 6,554,788 | B1 | 4/2003 | Hunley et al. |
| 7,258,673 | B2 | 8/2007 | Racchini et al. |
| 2004/0030761 | A1 | 2/2004 | Takeuchi et al. |
| 2004/0167464 | A1 | 8/2004 | Ireland et al. |
| 2004/0259494 | A1 * | 12/2004 | Mazar ............................. 455/1 |
| 2006/0167381 | A1 | 7/2006 | Azer et al. |

FOREIGN PATENT DOCUMENTS

| | | |
|---|---|---|
| EP | 0 542 413 | 5/1993 |
| EP | 1022566 | 1/2000 |
| EP | 1022566 | 7/2000 |
| EP | 1 338 295 | 2/2003 |
| EP | 1 304 633 | 4/2003 |
| JP | 11-142411 | 5/1999 |
| JP | 4-313933 | 4/2001 |
| JP | 2002-282218 | 2/2002 |
| JP | 2002-282218 | 10/2002 |
| JP | 4-313933 | 8/2009 |
| WO | 98/32013 | 7/1998 |
| WO | 01/45774 | 11/2000 |
| WO | 01/42473 | 6/2001 |
| WO | 01/45774 | 6/2001 |
| WO | 2006001929 | 1/2006 |
| WO | 2006081103 | 8/2006 |

OTHER PUBLICATIONS

"Point-of-care: From Data Management to Information Management, Implementing Point of Care Connectivity", Christopher Fetters, AACC Experts on Line, Jun. 4, 2002.*
Extended European Search Report on a counterpart European patent application No. 11150647, mailed on Apr. 15, 2011, 6 pages.
International Search Report and Written Opinion of the International Search Authority for PCT/US2006/001614, Mailed on Jun. 16, 2006.
English translation of the Office Action issued in the Japanese counterpart Application No. 2012-193209 (4 pages).
A direction selective zone routing protocol for ad-hoc networks, IPSJ SIG technical reports, Yoshitaka Honma, vol. 2003, No. 87, p. 109-115, Information processing society of Japan, Sep. 17, 2003, (Full article, in Japanese, and an English abstract of the Japanese article is submitted herewith).
English translation of the Office Action issued in the Japanese counterpart Application No. 2012-193209 (4 pages), Jun. 25, 2013.
A direction selective zone routing protocol for ad-hoc networks, IPSI SIG technical reports, Yoshitaka Honma, vol. 2003, No. 87, p. 109-115, Information processing society of Japan, Sep. 17, 2003, (Full article, in Japanese, and an English abstract of the Japanese article is submitted herewith).
English translation of the Office Action issued in the japanese Counterpart Application No. 2007-553132 (5 pages).
English translation of the Office Action issued in the Japanese counterpart Application No. 2007-553132 (5 pages), Oct. 2, 2013.
Office Action (in Japanese) issued in the Japanese counterpart Application No. 2007-553132 (3 pages), Oct. 2, 2013.

* cited by examiner

METHOD AND SYSTEM FOR MANAGING PATIENT DATA

CROSS REFERENCE TO RELATED APPLICATION

This application is a divisional application of U.S. patent application Ser. No. 11/044,626, filed on Jan. 27, 2005 now U.S. Pat. No. 7,972,279, the entire contents of which are incorporated herein by reference.

FIELD OF THE INVENTION

The invention relates to a method and system for managing patient data. Specifically, the invention relates to an analytical instrument in direct communication with at least one other analytical instrument over a network for accessing patient data acquired by the other analytical instrument.

BACKGROUND OF THE INVENTION

Medical facilities such as hospitals and doctor's offices employ numerous medical devices to obtain and/or analyze samples from patients. These analytical instruments are often placed at different locations throughout the medical facility.

Typically, such instruments are connected to or communicate with a stand-alone computer to perform the data management functions relating to the processing of patient data. However, several problems exist with this arrangement. For example, the user must physically walk to the computer to see and/or manipulate the data from a particular device. In another example, the computer typically has a different user interface than the users interface of the instrument. Furthermore, in facilities using different instruments for different procedures, each instrument may have its own interface. These different user interfaces require the user to learn how to navigate through each user interface to perform the necessary tasks, and to quickly distinguish the differences between them. Moreover, if an analytical instrument is used outside of the facility in which it normally operates, the user would be unable to perform the data management functions without the stand-alone computer, or without having to return the instrument to the facility prior to performing any of these functions. This results in a cumbersome requirement to maintain the data management capabilities when the user travels with the instrument.

The medical facility may also employ a server computer for the storage of information associated with, for instance, the analytical data. The instruments (or other computers) traditionally communicate with the server to access the information. A user located at the server, however, cannot typically analyze a sample. Also, if many instruments request information from the server at approximately the same time, communications may be delayed. Moreover, if the server experiences a failure and has to be repaired, the retrieval of the data is delayed until the problem is fixed or until another server replaces the faulty server. Such server-centric arrangements can result in a chain reaction of inefficiencies such as data unavailability and inefficient medical treatment.

SUMMARY OF THE INVENTION

The present invention relates to a method, system, and apparatus for managing patient data. In one aspect, the invention relates to a system for managing patient data having many instruments. The instruments have a sampling member for sampling a body fluid from a patient and directly communicate with each other.

The direct communication can include a first instrument controlling a second instrument. The control can include, for instance, the first instrument calibrating the second instrument, the first instrument processing a sample on the second instrument, the first instrument turning the second instrument off, and/or the first instrument turning the second instrument on. The direct communication can include one instrument being in direct communication with at least two other instruments, and the communication can be unidirectional or bidirectional.

In one embodiment, the direct communication includes one instrument accessing patient data acquired by another instrument. The accessing of patient data can include viewing status of another instrument, viewing one or more operations on another instrument, and searching patient results on at least one other instrument. In one embodiment, one instrument can operate as an agent for one or more of the other instruments, and thereby can transmit to and receive data from another instrument subsequent to the other instrument acquiring and/or accessing patient data.

In some embodiments, the system also includes a single user interface for managing the analysis of the body fluid sample and patient data. The data acquired or stored in each instrument can be displayed in a common format.

In another aspect, the invention relates to an instrument having an analytical module, a data management module, and a communications module. The analytical module analyzes a body fluid sample. The data management module within the instrument enables management of data associated with the body fluid sample. The communications module facilitates instrument-to-instrument communications. In some embodiments, the instrument also includes a user interface for receiving user instructions relating to the analytical module, the data management module, and the communications module. In one embodiment, the management of data includes generating a report, (which, in some cases may be generated automatically) managing security information, performing competency testing, determining a pattern associated with the instrument, performing inventory management, quality control, and/or determining the workload of the instrument.

The data can include patient data, which may be combined with the analytical data associated with the analysis of the body fluid sample. The report can include a quality control report, a regulation report, and a workload report. Moreover, the report can be automatically generated. In one embodiment, the performance of competency testing can be determining a pattern of occurrences to facilitate better training.

In yet another aspect, the invention relates to a method for accessing patient data. The method includes connecting the instruments to a network. Each instrument includes a sampling member for sampling a body fluid from a patient. The method also includes the steps of sampling, by the sampling member of a first instrument, a body fluid from a patient and accessing, and analyzing the sample. A second instrument then accesses the results of the analysis directly from the first instrument. In some embodiments, an instrument initiates a configuration process on one or more of the plurality of instruments according to predetermined acceptable ranges of the results of the analysis.

In another aspect, the invention relates to a system for managing patient information including a collection of instruments, each instrument including a sampling member for sampling a body fluid. The system also includes a collection of communications modules, each communication module being associated with an instrument, and directly exchanging patient information with other instruments without the patient information being permanently stored or processed on an apparatus other than one of the instruments.

DETAILED DESCRIPTION

Figure 1:
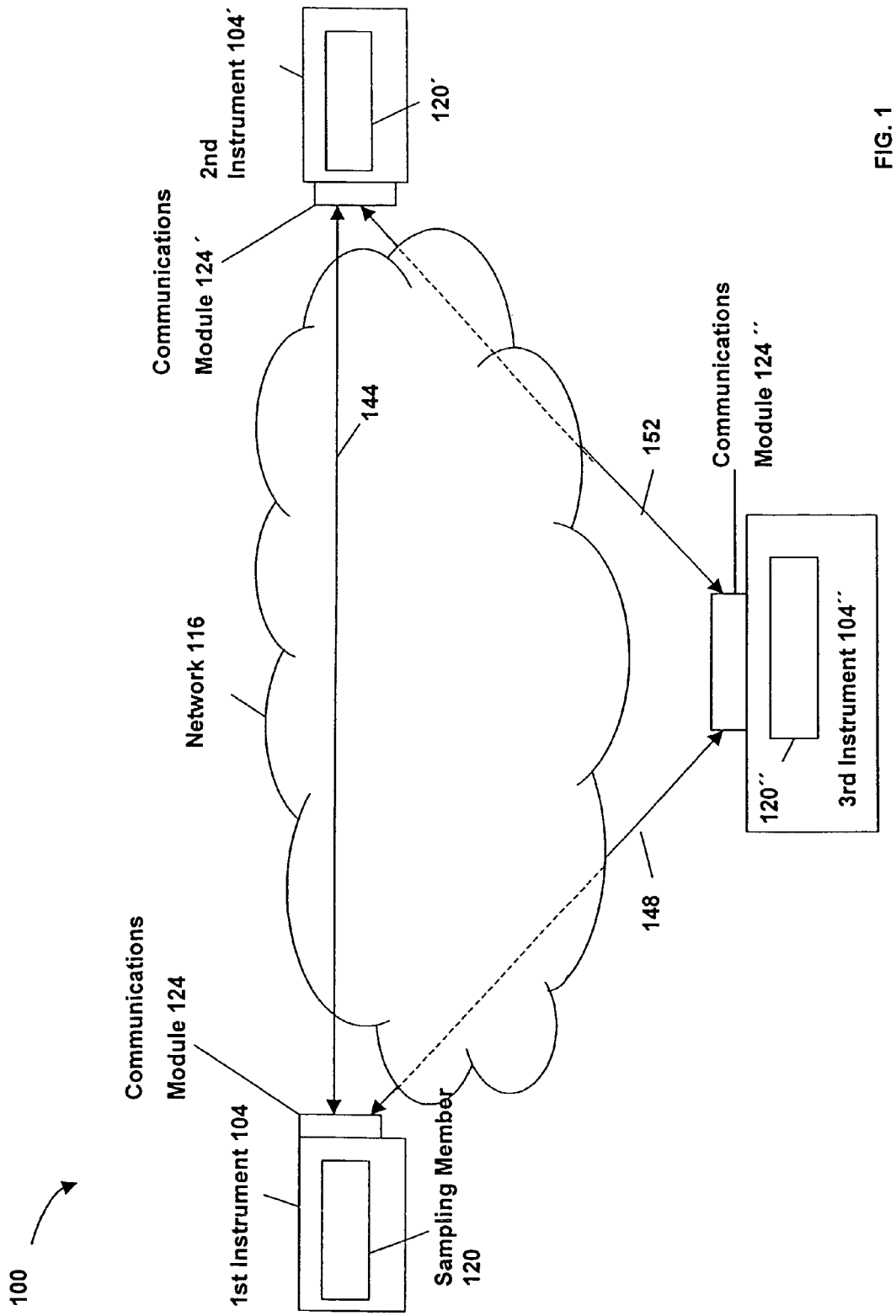
FIG. 1 is a block diagram of a system having a first, second, and third instrument communicating over a network according to an illustrative embodiment of the invention.

FIG. 1 is a block diagram of a system 100 having a first instrument 104, a second instrument 104', and a third instrument 104" (generally instrument 104) communicating over a network 116 according to an illustrative embodiment of the invention. Examples of instruments 104 include but are not limited to a GEM Intelligent Quality Management (iQM) 3000 analyzer, a GEM Intelligent Quality Management (iQM) 4000 analyzer (both from Instrumentation Laboratory, Lexington, Mass.), and a VITROS DT60 II Chemistry System (Johnson & Johnson, Piscataway, N.J.). Other instruments may be, for example, a hand-held instrument such as a handheld glucose sensor. The instruments 104 can be located in, for instance, a hospital, a doctor's office, a medical facility, a patient's home, an elderly care facility, an ambulance, public transportation vehicles, large public venues, or any other location in which medical analysis and/or patient data sampling occurs on either a routine or emergency basis. For example, one instrument of the system may be located in a hospital, and another one of the instruments may be located in a doctor's office. Alternatively, all of the instruments may be located in a hospital, but at remote locations throughout the hospital. In some cases, the instruments 104 travel throughout the facility, thereby introducing the possibility that any instrument 104 could be at any location at any time. Each instrument 104, 104', 104" includes a respective sampling member 120, 120', 120" (generally sampling member 120). An example of a sampling member 120 is a probe for contacting the sample, an inlet port for receiving a sample, a receptacle for receiving a sample cartridge, or a sample cuvette, for example. Each sampling member 120, 120', 120" can sample a body fluid from a patient. Examples of a body fluid include blood, serum, plasma, urine, semen, saliva, tracheo-bronchial washing, cerebrospinal fluid, and the like. The sampling member 120, 120', 120" can analyze a body fluid to determine qualitatively or quantitatively the amount or presence of one or more target analytes in the body fluid. Although described below with respect to the first instrument ("instrument 104"), the description applies to any or all of the instruments 104, 104', 104". Similarly, although the description below is with respect to the first sampling member 120 ("sampling member 120"), the description applies to any or all of the sampling members 120, 120', 120".

As used herein, accessing patient data means one instrument 104 directly accessing data on another instrument 104', i.e., a central processing unit (CPU) or server positioned between the first and second instruments 104, 104', respectively, is not necessary for the first and second instruments to access data from each other. Acquiring patient data means when one instrument 104 analyzes a target component in a patient body fluid sample. In one embodiment, the acquiring of patient data includes using the sampling member 120 to obtain a patient sample. Patient data is patient personal data and patient clinical data. Personal data can include, for example, name, gender, residence, age, height, weight, sex, allergies, and/or health history. Clinical data can include a qualitative or quantitative determination of a target analyte in a patient body fluid sample.

As used herein, direct communication between two instruments 104, 104' means one instrument 104 communicating with another instrument 104 without the aid of a central CPU or computer that is incapable of sampling a body fluid from a patient (i.e., that is not an instrument 104) and that provides additional data processing functionality with respect to the analysis, storage, display, or manipulation of the data other than devices such as routers, repeaters, or switches that manage, direct, and/or amplify messages over the network 116. Examples of direct communication among the instruments 104 includes, but is not limited to peer-to-peer communications, and communications over a mesh-type network whereby one or more of the instruments 104 can also assist with the transmission of a message from a first instrument 104 to a second instrument 104'.

To facilitate the direct communications among the instruments 104, each instrument 104 contains or is connected to (either permanently or on an ad hoc basis) a communication module 124. The communication module 124 maintains identification and routing information related to the plurality of instruments within the system, and packages instructions, data and other information as messages in such a manner that when broadcast, the message contains the routing information necessary to reach its intended destination (i.e., a second instrument 104') without the aid of a central server. The communications module 124 also receives messages, and decodes, decrypts, and/or compiles the message into instructions for the second instrument 104'. In some embodiments, the communications module 124 also provides confirmation messages back to the first instrument 104 to confirm that a message has beep received, understood, and/or acted upon.

With continued reference to FIG. 1, the direct communication between the first instrument 104 and second instrument 104' is shown with a first communications channel 144. Similarly, the direct communication between the first instrument 104 and third instrument 104" is shown with a second communications channel 148. Moreover, the direct communication between the second instrument 104' and third instrument 104" is shown with a third communications channel 152.

The network 116 can be, for instance, an intranet. Example embodiments of the communication channels 144, 148, 152 include standard telephone lines, LAN or WAN links (e.g., T1, T3, 56 kb, X.25), broadband connections (ISDN, Frame Relay, ATM), and wireless connections (802.11).

With continued reference to FIG. 1, the direct communication between, for instance, the first instrument 104 and the second instrument 104' enables the first instrument 104 to access patient data acquired by the second instrument 104'.

Likewise, the direct communication between the other instruments 104 enables one instrument (e.g., the second instrument 104') to access patient data acquired by another instrument (e.g., the third instrument 104") in direct communication with the instrument 104 (e.g., the second instrument 104'). In one embodiment, the direct communication between two or more instruments 104 is bidirectional. For example, when the first and second instruments 104, 104' are in direct communication, the first instrument 104 can communicate with and obtain information from the second instrument 104' and the second instrument 104' can likewise communicate with and obtain information from the first instrument 104. In another embodiment, the direct communication is unidirectional such that the first instrument 104 can communicate with and obtain information from the second instrument 104' but the second instrument 104' cannot initiate communications with and obtain information from the first instrument 104. Thus, independent of which instrument's sampling member 120 samples a patient's body fluid, any instrument 104 communicating over the network 116 can access data associated with the body fluid directly from the instrument 104 that sampled the body fluid.

Figure 2:
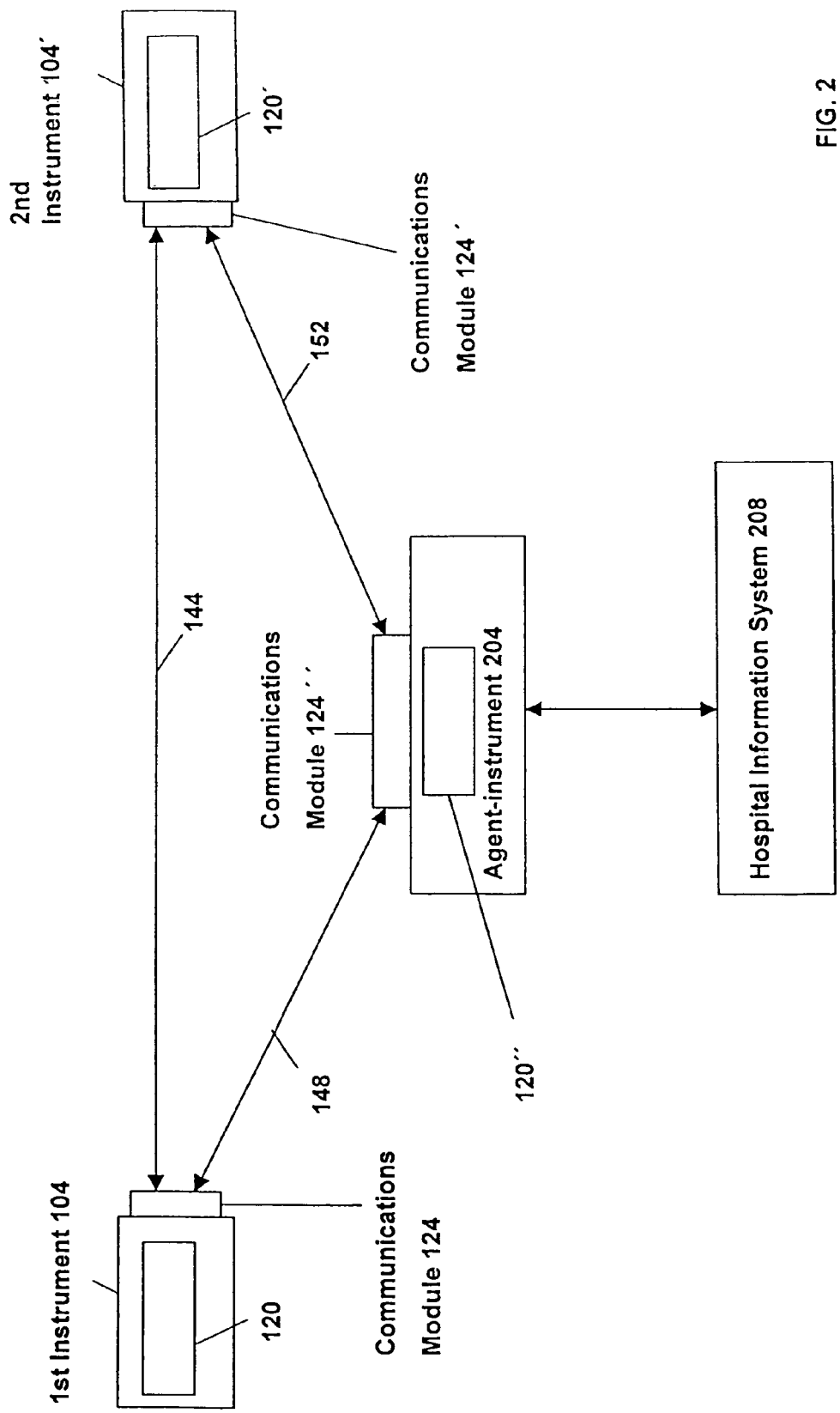
FIG. 2 is a block diagram of a system having a server communicating with a first and second instrument over a network according to an illustrative embodiment of the invention.

FIG. 2 is a block diagram of a system operating in such a manner that an agent-instrument 204 communicates with the first instrument 104 and the second instrument 104' over a network according to another illustrative embodiment of the invention. In one embodiment, the agent-instrument 204 acts as an agent for the first instrument 104 and the second instrument 104', i.e., the agent-instrument 204 can perform the functions that can be performed on the first and second instruments 104 and 104'. For example, the agent-instrument 204 stores the clinical data associated with a sample obtained by a sampling member of one or more of the instruments 104. Thus, in one embodiment, the agent-instrument 204 enables an instrument 104 to access patient data acquired by another instrument 104 by storing the patient data in a database and performing other centralized data processing functions. Thus, when a sampling member 120 samples a body fluid from a patient, the instrument 104 stores the patient data obtained from the sample. Additionally, the instrument 104 that acquired the sample also transmits the patient data to the agent-instrument 204. The agent-instrument 204 enables the other instruments 104 to access all patient data from a single instrument (rather than having to access patient data at all instruments 104 that sampled a sample from the patient). Alternatively, instruments 104 can communicate with the instrument 104 that sampled the patient's body fluid to obtain data associated with the body fluid.

In one embodiment, the agent-instrument 204 also transmits the patient data to a hospital information system 208. For example, the agent-instrument 204 transmits the patient data to the hospital information system 208 through a laboratory information system (LIS) interface. The hospital information system 208 can be, for example, another computer in the same (or different) hospital as the medical facility where the instruments 104 are located. The hospital information system 208 maintains a patient database for the hospital's patients. The agent-instrument 204 may also retrieve information from the hospital information system 208.

In one embodiment, one instrument 104 (e.g., the first instrument 104) directly communicates with another instrument 104 (e.g., the second instrument 104') to control the instrument (e.g., the second instrument 104'). If, for instance, the first instrument 104 is controlling the second instrument 104', the first instrument 104 calibrates the second instrument 104', initiates the processing of a patient sample on the second instrument 104', turns the second instrument 104' on, and/or turns the second instrument 104' off. The first instrument 104 can also control the second instrument 104' by initiating a specific measurement of an analyte in the patient sample.

Additionally, in one embodiment, the first instrument 104 controls a heterogeneous second instrument 104', i.e., the second instrument 104' is a different model or type compared with the first instrument 104. For example, in one embodiment the first instrument 104 is a GEM Intelligent Quality Management (iQM) 4000 analyzer and the second instrument 104' is a GEM Intelligent Quality Management (iQM) 3000 analyzer (both from Instrumentation Laboratory, Lexington, Mass.). Moreover, in one embodiment the first instrument 104 controls a second instrument 104' that is manufactured by a different company altogether. For example, the first instrument 104 is a GEM iQM 4000 analyzer and the second instrument 104' is a VITROS DT60 II Chemistry System (Johnson & Johnson, Piscataway, N.J.).

Figure 3:
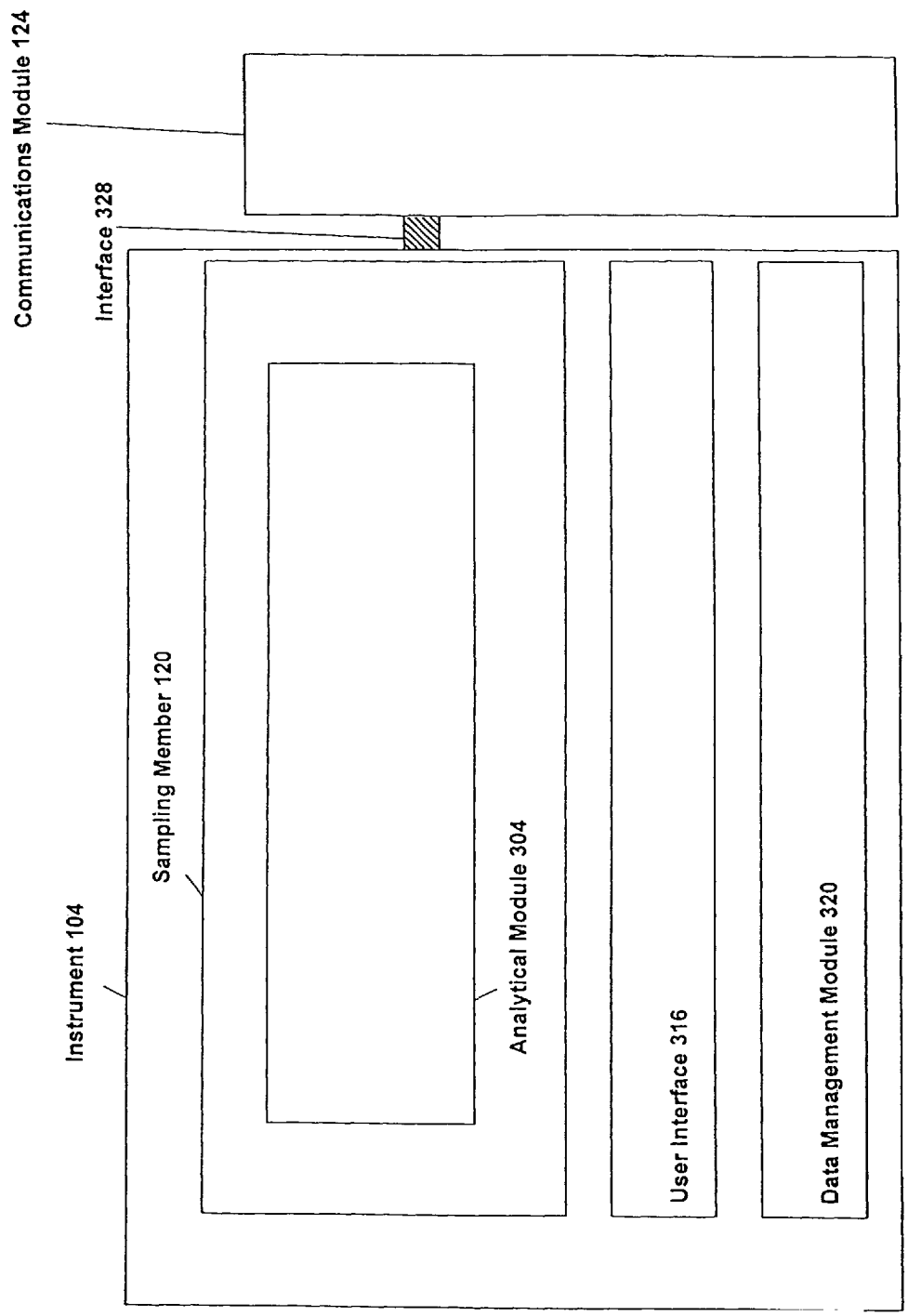
FIG. 3 is a block diagram of an instrument having a user interface and a data management module according to an illustrative embodiment of the invention.

FIG. 3 is a block diagram of an instrument 104 having a user interface 316 and a data management module 320 according to an illustrative embodiment of the invention. In the illustrated embodiment, the sampling member 120 of the instrument 104 has an analytical module 304 for analyzing patient data. In particular, the analytical module 304 is a software module providing a programmed series of steps that analyzes a target analyte in a body fluid sample from a patient. For example, the target analyte is blood platelet concentration, white blood cell concentration, red blood cell concentration, blood urea nitrogen (BUN), blood gases, electrolytes, metabolites, and/or hematocrit.

The instrument 104 also includes a user interface 316 and a data management module 320. The data management module 320 enables management of the patient data. The data management module 320 can manage patient data that is stored on the instrument 104 that the data management module 320 is executing on and/or can manage patient data stored on another instrument 104. For example, the data management module 320 of the first instrument 104 can perform management functions on data associated with a particular patient that the first instrument 104 accesses from the second instrument 104'.

The user interface 316 enables a user of the instrument 104 to perform functions associated with the analytical module 304 and the data management module 320. Specifically, the user interface 316 performs functions and displays patient data in a common format on the instruments 104. Thus, the user interface 316 enables the user of the instrument 104 to experience a single "look and feel" when sampling a body fluid sample, analyzing the sample, and/or managing patient data regardless of the instrument. As an example, a common menu structure can be employed such that the messaging functions all appear under one menu option that is consistent across all instruments 104, and operational functions such as processing a patient sample can be described using common terminology, with like screen coloring, command controls, and help text. The analytical module 304, the user interface 316, and the data management module 320 are software modules that can be written in any computer programming language, such as Java or C++. In some embodiments where the instruments 104 are manufactured by different vendors, a browser-like interface may be included as the user interface 316, thus enabling the use of standard data rendering, data transmission, and data presentation technologies such as HTML, HTTP/HTTPS, XML, SOAP, Web Services, and the like. Examples of browser interfaces include, but are not limited to applications such as Internet Explorer, by MIRCOSOFT CORPORATION of Redmond, Wash., NETSCAPE NAVIGATOR, by AOL/TIME WARNER of Sunnyvale, Calif., and MOZILLA FIREFOX by the MOZILLA FOUNDATION of Mountain View, Calif.

The user interface 316 enables a user to, for example, view a snapshot of the instrument screen display, review patient data or quality control results, review the instrument's status, enable or disable analytes, enable or disable operator access, lock the instrument 104, calibrate the instrument 104, configure the instrument 104 according to predetermined acceptable ranges of the results of the analysis of the patient data, and/or post a message on the instrument 104. Moreover, the user of an instrument 104 can use the user interface 316 to perform these functions on any other instrument (e.g., the second instrument 104'). Thus, a user can use the user interface 316 to view patient data acquired by the instrument 104 including the user interface 316 or another instrument 104, view the status of this or another instrument 104, view operations performed on this or another instrument 104 (e.g., analyze a patient sample, prepare a pie chart for all patient data for a particular patient, etc.), and/or search patient results on this or another instrument 104. As described above, the instruments 104 may be heterogeneous types, e.g., instruments manufactured by different companies altogether.

Examples of data management functions that the data management module 320 can perform include generating a report, managing security information, performing competency testing, and determining the workload of the instrument 104. For instance, the data management module 320 can automatically generate a table of the previous ten data points obtained for a target analyte of a patient's body sample. The data management module 320 can also generate a report (e.g., a table) on demand or periodically as based on a predetermined schedule. The user of the instrument 104 can also use the data management module 320 to search for patterns, such as a pattern in a patient's clinical data. Moreover, the user can additionally use the data management module 320 to discern data patterns associated with one or more instruments 104. For example, the data management module 320 can determine that a particular instrument, such as the third instrument 104", has the highest number of analytical failures.

Further, the data management module 320 can provide operator competency information. For example, the data management module 320 of the first instrument 104 may determine that the third instrument 104" has the highest number of discarded samples. Such information may be useful in assessing operator performance. The operator using the third instrument 104" may, in such cases, require additional training in the use of the instruments 104.

Additionally, the data management module 320 can perform inventory management. For example, if the sampling member 120 employs cartridges to sample a patient's body fluid, the data management module 320 can determine the number of times the cartridge has been used and indicate when a user of the instrument 104 needs to replace the cartridge. Further, the data management module 320 of one instrument 104 (e.g., the first instrument 104) can determine when the cartridge supply of another instrument (e.g., the second instrument 104') needs to be replaced.

As described above, the data management module 320 can also determine the workload of an instrument 104. In one embodiment, the data management module 320 can determine the workload of the instrument 104 that the data management module 320 is executing on. The data management module 320 can also determine the workload of another instrument 104 communicating with the instrument 104 that the data management module 320 is executing on. For example, a user of the first instrument 104 can use the data management module 320 to determine the frequency that the third instrument 104" is being used (e.g., once a day, ten times a day, etc.). The user can use this information to determine whether to remove an instrument 104 (e.g., the third instrument 104") from the particular location (e.g., if the instrument 104 is not being used enough to warrant its positioning at the location), to add another instrument 104 to the same location (e.g., if the instrument 104 is being overworked) or to regulate the distribution and usage of the instruments 104.

In a particular embodiment, a user can access the user interface 316 and the data management module 320 from a web browser (e.g., Internet Explorer developed by Microsoft Corporation, Redmond, Wash.). For instance, a user can use the web browser executing on a personal computer (e.g., in the user's office in the hospital) to access the data management module 320 and/or the user interface 316. Moreover, the user interface and data management module displayed in the web browser have the same "look and feel" as the user interface 316 and data management module 320 executing on the instrument 104. The web browser enables a remote user to perform the same functions that a user using the user interface 316 on the instrument 104 can perform. Thus, a remote user can, for instance, view a snapshot of the instrument screen display, review patient or quality control results, review the instrument's status, enable or disable analysis, enable or disable operator access, lock the instrument, calibrate the instrument 104, and post a message on the instrument 104.

Continuing to refer to FIG. 3, and as described above with reference to FIG. 1, each instrument 104 comprises a communications module 124 to facilitate inter-instrument communication. In some embodiments, the communications module 124 is an internal component of the instrument 104 that (i.e., an internal wireless network interface card, transponder, or other signal-generating device). In other embodiments the communications module 124 is an external device that, for example, can be periodically connected to the instruments 104 via an interface 328.

Figure 4:
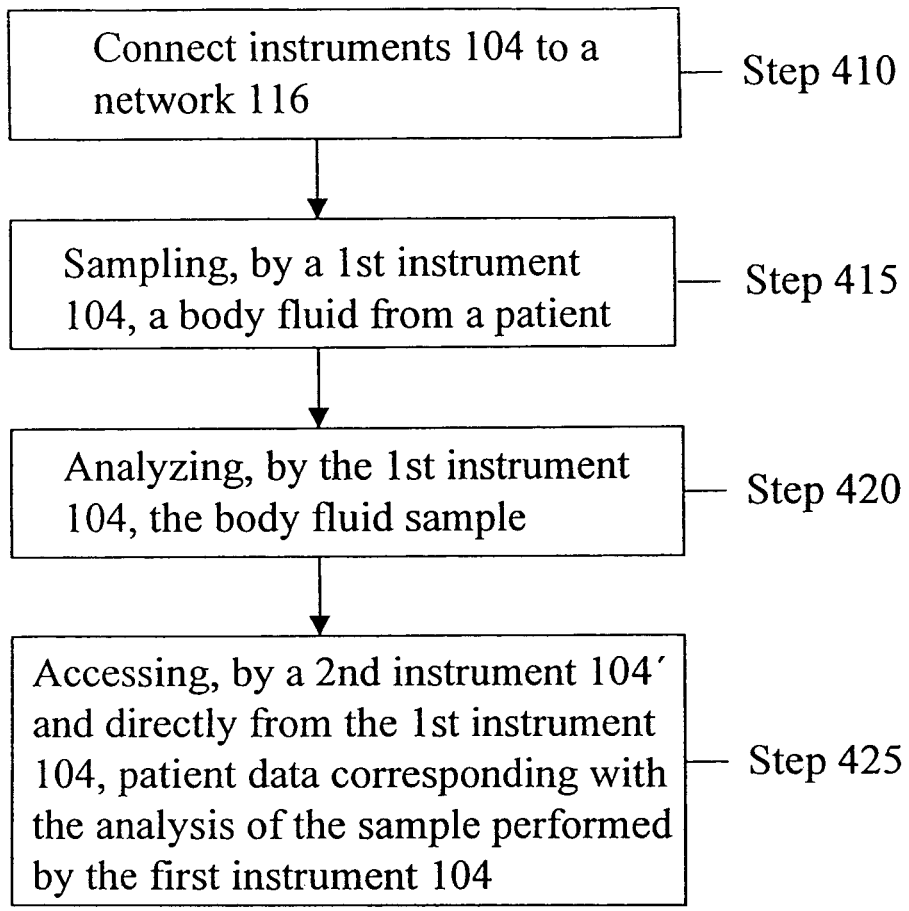
FIG. 4 is a flow diagram of the steps performed for configuring the instruments of FIG. 1 according to an illustrative embodiment of the invention.

FIG. 4 is a flow diagram of the steps performed for configuring the instruments 104 of FIG. 1 according to an illustrative embodiment of the invention. The instruments 104 in the illustrative embodiment are connected to the network 116 so that each instrument 104 is in direct communication with one or more of the other instruments 104 (step 410). The sampling member 120 of the first instrument 104 then samples a body fluid from a patient (step 415). The first instrument 104 then analyzes the body fluid sample (step 420) and obtains patient data. The second instrument 104' (or any other instrument 104) then accesses, directly from the first instrument 104, the patient data corresponding with the analysis of the sample (step 425). Alternatively, the second instrument 104' instructs the first instrument 104 to sample a body fluid and steps 415, 420, 425 are then started. For example, upon receipt of the instruction, the first instrument 104 samples a body fluid (e.g., blood) from a patient, as shown in step 415. Moreover, any number of the steps shown in FIG. 4 may occur. For instance, the first instrument 104 may only sample a body fluid (Step 415) and then analyze the body fluid sample (Step 420). Another instrument 104 may not access patient data associated with the analysis of the sample or may access the patient data after a long time delay (e.g., four days later).

Figure 5:
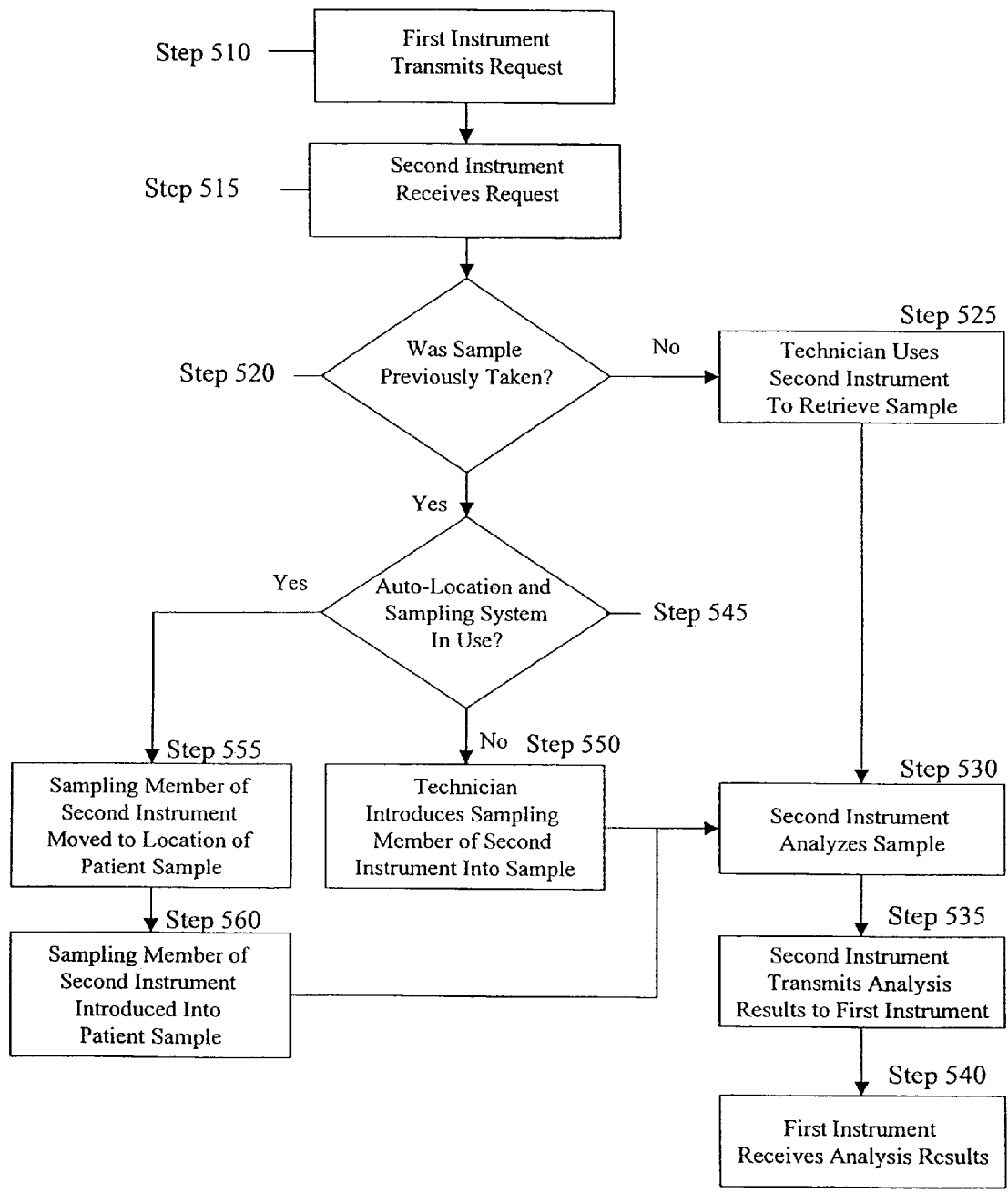
FIG. 5 is a flow diagram of the steps performed for using the instruments of FIG. 1 according to an illustrative embodiment of the invention.

With reference to FIG. 5, and in one exemplary embodiment, a laboratory technician needing a particular test, analysis, or collection of a patient sample utilizes a first instrument 104 to initiate a request for a patient sample (STEP 510). A doctor, nurse, or other medical technician receives the request on a second instrument 104' (STEP 515). The request may be in the form of a screen message, audible message, or other recognizable indication that a request has been received. The medical technician may then acknowledge receipt of the request and, if no sample was previously taken (STEP 520) draw the patient sample using the sampling member of the second instrument 104' (STEP 525) after which the second instrument 104' then performs the requested analysis (STEP 530). The second instrument 104' then transmits the results of the analysis (STEP 535) where it is received by the first instrument 104 (STEP 540), thereby providing the laboratory technician with the necessary data. Such requests may be made in conjunction with scheduled rounds, patient care protocols, or on an as needed (i.e., random) basis.

In another embodiment a medical technician tending to a patient and using a first instrument 104 requests an analysis of a previously drawn sample of the patient. At another location, such as a laboratory where multiple patient samples are stored awaiting analysis, the second instrument 104' receives the request from the first instrument 104 and introduces the sampling member of the second instrument 104' into the patient sample (STEP 550). The analysis is conducted by the second instrument 104' (STEP 530), and the results are transmitted from the second instrument 104' (STEP 535) back to the first instrument 104 (STEP 540), where the results are displayed. Alternatively, or in conjunction with this approach, the patient samples are arranged in a tray such that an automated sampling member probe of the second instrument 104' extends to and selects the desired patient sample and samples the patient sample (STEP 560) such that the appropriate analysis of the sample directed by the first instrument 104 is conducted by the second instrument 104' (STEP 530).

In another example, the second instrument 104' may be connected directly to a patient via an extracorporeal device such as a blood pump used during a cardio-bypass procedure. In such cases, the sampling member of the second instrument 104' is in contact with the patient sample on a frequent, or in some cases continuous basis, and requests for sampling and analysis by the first instrument 104 directed by the second instrument 104' can be serviced in real-time.

Having described certain embodiments of the invention, it will now become apparent to one of skill in the art that other embodiments incorporating the concepts of the invention may be used.

What is claimed is:

1. A method for accessing patient data, the method comprising:
   (a) providing a plurality of instruments configured for direct communication there between to a network, each instrument comprising a sampling member for contacting a body fluid sample from a patient and acquiring patient data therefrom;
   (b) communicating via a communications module for facilitating direct electronic bidirectional communication between a first instrument and a second instrument in the plurality of instruments wherein the direct electronic bidirectional communication comprises controlling the first instrument by the second instrument and controlling the second instrument by the first instrument;
   (c) processing by the first instrument the body fluid sample, wherein the second instrument is controlling said processing; and
   (d) accessing, by the second instrument directly from the first instrument, the acquired patient data.

2. The method of claim 1, wherein the first instrument in electronic bidirectional communication with the second instrument accesses acquired patient data acquired by the sampling member on the second instrument using the communication module of the first instrument.

3. The method of claim 2, wherein the acquired patient data comprises an analyzed target component of said patient's body fluid.

4. The method of claim 1, wherein the first instrument in the plurality of instruments is in electronic bidirectional direct communication with at least the second instrument and a third instrument in the plurality of instruments.

5. The method of claim 1, wherein the sampling member further comprises an analytical module for analyzing a target component in the body fluid sample.

6. The method of claim 1, wherein the first instrument in the plurality of instruments further comprises a user interface comprising a display for operator management of the analysis of the body fluid sample and for operator management of patient data.

7. The method of claim 6, wherein the display of the acquired patient data by first instrument displays information in a format that is common to the plurality of instruments and is directly accessible by the second instrument in the plurality of instruments.

8. The method of claim 1, wherein the direct electronic bidirectional communication between the first instrument and the second instrument is without the aid of a server.

9. The method of claim 1, wherein the sampling member of at least one of the plurality of instruments analyzes a first analyte and the sampling member of another of the plurality of instruments analyzes a second analyte.

10. The method of claim 1, wherein the first instrument further comprises a display for viewing of electronic data, wherein the electronic data is selected from the group consisting of viewing status of the second instrument on the display of the first instrument, viewing operations of the second instrument or viewing operations of the first instrument on the display of the first instrument, and viewing acquired patient data on the second instrument or on the first instrument or on the display of the first instrument.

11. The method of claim 9 wherein the first acquired patient data is displayed using a browser application on the display.

12. The method of claim 1, wherein the plurality of instruments is members of a peer-to-peer electronic communications network.

13. The method of claim 1, wherein the plurality of instruments are members of a mesh-type electronic communications network.

14. The method of claim 1, wherein at least one of the plurality of instruments is configured to assist with transmission of electronic, communications messages between two other of the plurality of instruments.

15. The method of claim 1, wherein the communications module maintains identification information related to the plurality of instruments.

16. The method of claim 1, wherein the communications module packages information as electronic communications messages.

17. The method of claim 1, wherein the communications module receives, decodes, and decrypts electronic communications messages.

18. The method of claim 1, wherein the communications module confirms that electronic communications messages have been received.

19. The method of claim 1, wherein the communications module comprises routing information comprising information in a communication message necessary for the communication message to reach its intended destination.

20. The method of claim 1, wherein the control of the first instrument by the second instrument comprises calibrating the first instrument.

21. The method of claim 20, wherein the control of the first instrument by the second instrument comprises initiating a measurement of an analyte in a patient sample on the first instrument.

22. The method of claim 1, wherein the control of the first instrument by the second instrument comprises the second instrument instructing the first instrument to analyze a sample.

23. The method of claim 1, wherein the control of the first instrument by the second instrument comprises the second instrument switching on the first instrument.

* * * * *